United States Patent [19]
Woolard

[11] Patent Number: 5,110,947
[45] Date of Patent: May 5, 1992

[54] PROCESS FOR THE PREPARATION OF 3-CARBOALKOXYPYRROLIDONES

[75] Inventor: Frank X. Woolard, Richmond, Calif.

[73] Assignee: ICI Americas Inc., Wilmington, Del.

[21] Appl. No.: 547,706

[22] Filed: Jul. 3, 1990

Related U.S. Application Data

[63] Continuation of Ser. No. 291,083, Dec. 27, 1988, abandoned.

[51] Int. Cl.⁵ .......................................... C07D 207/08
[52] U.S. Cl. ..................................................... 548/531
[58] Field of Search ......................................... 548/531

[56] References Cited

U.S. PATENT DOCUMENTS 4,874,422 10/1989 Woolard et al. ............... 544/141 X

OTHER PUBLICATIONS

C.A., vol. 54, (1960), 12107f to i., Perekalin et al.
C.A., vol. 57, (1962), 9778f to 9779g., Cologne et al..

Primary Examiner—Joseph Paul Brust
Attorney, Agent, or Firm—Michael J. Bradley

[57] ABSTRACT

The process of the present invention provides 3-carboalkoxypyrrolidones by the cyclization of a malonate, followed by reduction with hydrogen in the presence of a noble metal catalyst. The products are useful as intermediates for pesticides.

1 Claim, No Drawings

PROCESS FOR THE PREPARATION OF
3-CARBOALKOXYPYRROLIDONES

This is a continuation of application Ser. No. 291.083, filed Dec. 27, 1988, now abandoned.

BACKGROUND OF THE INVENTION

The present invention is related to the preparation of 3-carboalkoxypyrrolidones.

The compounds to be synthesized 3-carboalkoypyrrolidones of the formula

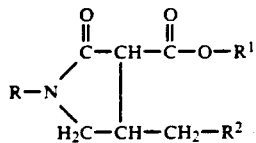

are useful as intermediates in the preparation of certain pesticides, and more particularly of certain herbicides.

Prior to the present invention, the primary method for synthesizing pyrrolidones used the reduction of a nitro group to an amine to form the 1,2-bond of the pyrrolidone ring. This method precludes the formation of a pyrrolidone ring in which the nitrogen atom is substituted with anything other than hydrogen. To substitute the nitrogen after the ring has been formed involves forcing conditions and the problem that the 3-position of the ring is more reactive.

A process has been described (Japanese publication JP 46/24381: CA 75(23):140709m) that allows for the introduction of a variety of substituents on the nitrogen. but it also results in mixtures of two different ring systems. In addition, to be useful as herbicide intermediates, the pyrrolidones that are formed must have the methylene group at the 3-position oxidized to a carboxylic acid and the carboxylic acid at the 4-position reduced to an alkyl group, a difficult and time-consuming procedure.

SUMMARY OF THE INVENTION

The process of the present invention provides 3carboalkoxypyrrolidones by the cyclization of a malonate, followed by reduction with hydrogen in the presence of a noble metal catalyst.

DETAILED DESCRIPTION OF THE INVENTION

More particularly, this invention is directed to a process for the manufacture of a compound having the formula

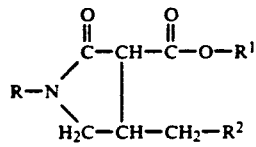

wherein,
R is lower alkyl, lower haloalkyl lower cycloalkyl, lower cycloalkylalkyl, benzyl, chlorobenzyl or the group

in which each of X and Y is independently hydrogen, halogen, lower alkyl, lower haloalkyl, lower alkoxy, lower haloalkoxy, lower alkylsulfinyl, lower haloalkylsulfinyl, lower alkylsulfonyl, lower haloalkylsulfonyl, phenoxy, substituted phenoxy, pyridyloxy, or substituted pyridyloxy;
$R^1$ is hydrogen or lower alkyl and
$R^2$ is hydrogen or lower alkyl:
which process comprises
a) reacting a compound having the formula

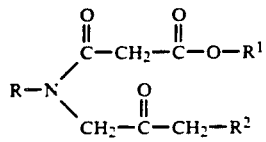

wherein R, $R^1$ and $R^2$ are as defined above, with a moderate or a strong base, followed by acidification to give a pyrroliden-2-one of the formula

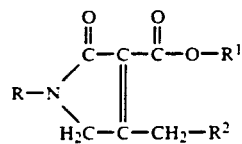

and,
b) reducing the compound of formula III with hydrogen gas in the presence of a noble metal catalyst to produce a compound of formula I.

Any strong or moderate base which will effect the desired result may be used in the present invention. Such bases are selected from those in the range of pK 9-18 and which are not nucleophilic. Examples include sodium hydride, pyridine and substituted pyridines, tertiary amines such as triethylamine, and the salts of tertiary alcohols such as tert-butoxide. For maximum efficiency, the reaction is preferably run using n excess of the base. While the mount of excess is a matter of choice, the reaction may conveniently be run at an excess of up to about 20% of base.

The selection of the acid and its amount for the acidification step in reaction a) is any acid and amount which is sufficient to effect spontaneous elimination of water from the intermediate to give the pyrroliden-2-one (III).

A noble metal catalyst may be chosen from those comprising gold, silver, platinum, iridium, rhodium, ruthenium or palladium chemically bound with other elements in the form of metal-containing compounds such as salts and oxides. The metal-containing compounds can also be present in the form of complexes with common complexing agents, examples of which re triphenylphosphine and carbon monoxide. Advantageously, the noble metal catalysts are selected from those comprising platinum or palladium. Examples include palladium on carbon and platinum oxide. Platinum oxide is preferred. The noble metal catalysts may be used singly or as mixtures.

The noble metal catalyst is present in the reaction in a catalytic amount. The quantity which will constitute a "catalytic amount" will be any quantity that serves to increase the rate of reaction, with larger quantities providing a greater increase. The quantity used in any particular application will be determined in large part by the individual needs of the manufacturing facility. Factors which enter into such a determination include the catalyst cost, recovery costs, desired reaction time, and system capacity. Aside from these considerations, the catalyst quantity is not a critical feature of the invention and can vary over a wide range. It will be most convenient to use an amount of catalyst which comprises from about 0.01 to about 20.0 mole percent, preferably from about 0.1 to about 10.0 mole percent based on the pyrroliden-2-one of formula III.

The process may successfully be run over a wide range of temperatures. The operating temperature may range rom about 10° C., to about 40° C.

The process does not have a critical operating pressure, but is operable over wide pressure range, subject only to considerations of time economy, process convenience and materials of construction. It is most convenient, however, to conduct the reaction a) at approximately atmospheric pressure. It is most convenient to conduct the reaction b) at a pressure of from about 0 to about 60 psig, preferably from bout 5 to about 60 psig, and more preferably of about 35-55 psig.

A variety of solvents can be used in the practice of the present invention. Any inert solvent can be used, including, but not limited to the following: aliphatic compounds, for example hexane or octane; aromatic compounds, for example benzene, toluene, xylene or mesitylene; chlorinated aliphatic or aromatic compounds, for example methylene chloride, ethylene dichloride or chlorobenzene; ethers, for example 1,2-dimethoxyethane, diethyl ether, tetrahydrofuran (THF) or 1,4-dioxane; alcohols, for example isopropanol or ethylene glycol; ketones, for example acetone, methyl ethyl ketone or methyl isobutyl ketone; amides, for example N,N-dimethylformamide or N-methylpyrrolidinone; nitriles, for example acetonitrile or butyronitrile; and carboxylic acids and their esters, for example acetic propionic or butyric acid or ethyl acetate.

The 3-carboalkoxypyrrolidones produced by the reaction of the invention can be recovered from the reaction mixture by any conventional technique.

As used in this specification and the attached claims:

The term "lower alkyl" refers to an alkyl group, straight or branched, of one to six carbon atoms.

The term "lower cycloalkyl" refers to a cycloalkyl group of three to seven carbon atoms.

The term "lower cycloalkylalkyl" refers to a lower alkyl group substituted with a lower cycloalkyl group, the total number of carbon atoms being from four to eight.

The term "lower alkoxy" refers to an alkoxy group, straight or branched of one to six carbon atoms.

The term "lower alkylsulfinyl" refers to an alkylsulfinyl group, straight or branched of one to six carbon atoms.

The term "lower alkylsulfonyl" refers to an alkylsulfonyl group, straight or branched, of one to six carbon atoms.

The terms "lower haloalkyl", "lower haloalkoxy", "lower haloalkylsulfinyl" and "lower haloalkylsulfonyl" refer to a lower alkyl group, a lower alkoxy group, a lower alkylsulfinyl group, and a lower alkylsulfonyl group, respectively, substituted by one or more halogen atoms. Such halogen is preferably fluoro.

The terms "substituted phenoxy" and "substituted pyridyloxy" refer to a phenoxy group and a pyridyloxy group, respectively, substituted at one to five of the carbon atoms with groups such as halogen, lower alkyl, lower haloalkyl, lower alkoxy or lower haloalkoxy.

Where any of the substituents R, X and Y is or comprises halogen, such halogen is conveniently selected from bromo, chloro or fluoro.

Within the scope of the above description, certain embodiments are preferred.

In R, the phenyl group substituted with X and Y is preferred.

Conveniently, X and Y are selected from hydrogen, halogen, $C_{1-4}$ alkyl, trifluoromethyl trifluoromethylsulfinyl, and trifluoromethylsulfonyl. In X, bromo, chloro, $C_{1-4}$ alkyl, and trifluoromethyl are preferred, and trifluormethyl is more preferred. In Y, hydrogen and $C_{1-4}$ alkyl are preferred, and hydrogen is more preferred.

In $R^1$, hydrogen and $C_{1-4}$ alkyl are preferred, and hydrogen, methyl and ethyl are more preferred.

In $R^2$, hydrogen and $C_{1-4}$ alkyl are preferred, and methyl is more preferred.

The starting malonate of formula II is prepared by the acylation of a ketone of formula IV with an alkyl malonyl chloride of formula V, in the presence of a base such as pyridine and at a preferred temperature range of from about 5° C. to about 10° C.

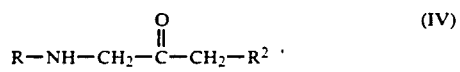

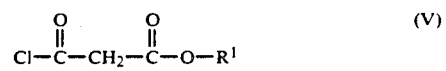

The ketone of formula IV is prepared by the reaction of the corresponding alcohol (VI) with a reagent that will form a carbamate, is can be accomplished with a variety of alkyl chloroformates or anhydrides and is preferably conducted with di-t-butyldicarbonate. The reaction can be conducted without solvent, at between 80° C., and 100° C. The resulting carbamate is then oxidized to the ketone under basic to neutral conditions using either aqueous sodium hypochlorite or pyridine dichromate in refluxing methylene chloride. The ketone is treated with anhydrous HCl gas to give the hydrochloride of the ketone (IV).

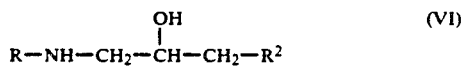

The alcohol of formula VI is known (see, e.g. U.S. Pat. No. 4,723,986) or, in those cases where it may not be known, can be synthesized by procedures known in the art.

The process of the present invention is further illustrated by the following examples. These examples are offered strictly for purposes of illustration, and are not intended to either limit or to define the invention.

EXAMPLE 1

This example illustrates the preparation of N-(2-oxo)-butyl-3-aminobenzotrifluoride hydrochloride.

A mixture of N-(2-hydroxy)butyl-3-aminobenzotrifluoride (106.86 g, 0.458 mol) and di-t-butyl dicarbonate (110.0 g, 0.504 mol), under N₂, was heated on a steam bath with occasional swirling. After 10 hours, gas evolution had ceased. The crude product was then combined with ether 300 mL), washed with water (3×250 mL) and with saturated NaCl solution (1×250 mL), and dried over Na₂SO₄, after which the solvent was removed in vacuo to give N-(2-hydroxy)butyl-N-t-butoxycarbonyl-3-aminobenzotrifluoride (152.73 g 100%) as a thick colorless oil.

A suspension of pyridinium dichromate (86.14 g 0.229 mol), methylene chloride (200 mL), trifluoroacetic acid (7.70 g, 4.53 mL, 0.067 mol) and pyridine (4.75 g, 4.86 mL, 0.060 mol) stirred and heated to a gentle reflux. N-(2-hydroxy)butyl-N-t-butoxycarbonyl-3-minobenzotrifluoride (51.0 g, 0.153 mol) in 100 mL of methylene chloride was added dropwise over one hour. When the addition was complete, the refluxing was continued for another 8 hours. The heating was then discontinued and the stirring was continued overnight at room temperature. The suspension was then diluted with 400 mL of ether to precipitate the inorganic salts and was filtered through diatomaceous earth. Removal of the solvents under reduced pressure provided a dark oil that was flash chromatographed on silica gel with ether as eluent. The resulting tan oil was taken up in 400 mL of ether and rapidly stirred, and the solution was saturated at room temperature with anhydrous HCl gas. After stirring overnight, the precipitated product was isolated by vacuum filtration to yield 30.61 g (75) of N-(2-oxo)-butyl3-aminobenzotrifluoride hydrochloride as a white powder. m.p. 113° C., dec., the structure of which was confirmed by MR, IR and MS.

EXAMPLE 2

This example illustrates the preparation of ethyl N-(3-trifluoromethyl)phenyl-N-(2-oxo)butylamalonate monoamide.

A mixture of N-(2-oxo)butyl-3-aminobenzotri-fluoride hydrochloride (30.61 g, 0.114 mol), benzene (200 mL) and pyridine (20.61 mL, 2016 g, 0.255 mol) was stirred, placed in an ice bath and cooled to 5° C. Ethyl malonyl chloride (27.10 g, 0.180 mol) in 40 mL of benzene was then added at such a rate that the temperature did not rise above 10° C. When the addition was complete, the suspension was poured into 200 mL of water and the layers were separated. The organic phase was washed with water (3×150 mL), with 3% aq. HCl (1×150 mL) and with sat. NaCl solution (1×150 mL), and was dried over MgSO₄. The solvent was removed under reduced pressure to provide crude ethyl N-(3-trifluoromethyl)phenyl-N-(2-oxo)butylmalonate monoamide (43.31 g, 110%).

EXAMPLE 3

This example illustrates the preparation of 1-(3-trifluoromethyl)phenyl-3-carboethoxy-4-ethyl-Δ³,⁴-pyr-roliden-2-one.

A suspension of sodium hydride (4.28 g. 0.178 mol) and freshly distilled (from Na/benzophenone) THF (50 mL) was stirred, and a solution of crude ethyl N-(3-tri-fluoromethyl)-phenyl-N-(2-oxo)butylmalonate monoamide (43.31 g) in 140 mL of THF was added dropwise at such a rate that the evolution of hydrogen was controlled (ca. 20 min.). When the addition was complete, the stirring was continued for an additional 0.5 hour and then conc. HCl (100 mL) was added dropwise. Water (250 mL) was added, and the crude product was isolated by vacuum filtration. Recrystallization from a minimum volume of methanol gave 1-(3-trifluoromethyl)phenyl-3-carboethoxy-4-ethyl-Δ³,⁴-pyrroliden-2-one (32.55 g, 87% based on starting amount of aminoketone hydrochloride in Example 2) as thick, colorless prisms, m.p. 120°-126° C., the structure of which was confirmed by NMR, IR and MS.

EXAMPLE 4

This example illustrates the preparation of 1-(3-carboethoxy-4-ethyl-2-pyrrolidone.

To a hydrogenation bottle was added platinum oxide (250 mg) and 1-(3-trifluoromethyl)phenyl-3-carboethoxy-4-ethyl-Δ³,⁴-pyrroliden-2-one (32.55 g, 99.4 mmol) in 150 mL of ethyl acetate. The bottle was placed on a Parr apparatus and evacuated/flushed with hydrogen three times. The hydrogen pressure was adjusted to 50 psi and the flask was shaken. Periodically, as the hydrogen was consumed the pressure was readjusted to 50 psi. When hydrogen uptake ceased, the catalyst was removed by vacuum filtration through a pad of diatomaceous earth and the ethyl acetate was removed under reduced pressure to give 1-(3-trifluoromethyl)phenyl-3-carboethoxy-4-ethyl-2-pyrrolidone (32.70 g, 100%) as a very pale yellow oil, the structure of which was confirmed by NMR, IR and MS.

Although the present invention has been described in some detail by way of example for purposes of clarity and understanding, it will be apparent that other arrangements and equivalents are possible and may be employed without departing from the spirit and scope of the invention. Therefore, the description and illustrations should not be construed as limiting the scope of the invention, which is delineated by the appended claims.

What is claimed is:
1. The compound having the formula

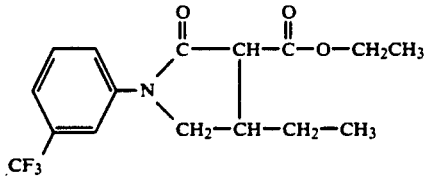

* * * * *